United States Patent [19]

Hoffmann et al.

[11] Patent Number: 5,230,887
[45] Date of Patent: Jul. 27, 1993

[54] IMMUNE SYSTEM STABILIZERS FOR PREVENTION AND THERAPY OF DISORDERS ASSOCIATED WITH IMMUNE SYSTEM DISFUNCTION

[75] Inventors: Geoffrey W. Hoffmann; Tracy A. Kion; Clayton A. Welder, all of Vancouver, Canada

[73] Assignee: Immune Network Research Ltd., Vancouver, Canada

[21] Appl. No.: 629,331

[22] Filed: Dec. 18, 1990

Related U.S. Application Data

[63] Continuation-in-part of Ser. No. 551,262, Jul. 11, 1990, abandoned.

[51] Int. Cl.$^5$ ............................................. A61K 39/00
[52] U.S. Cl. .................................... 424/85.8; 424/88
[58] Field of Search .................... 424/85.8, 88, 89; 514/8

[56] References Cited

U.S. PATENT DOCUMENTS

| | | |
|---|---|---|
| 4,719,107 | 1/1988 | Carosella et al. ............... 424/85.8 |
| 4,966,753 | 10/1990 | McMichael ......................... 424/88 |
| 5,004,604 | 4/1991 | Terness et al. .................... 424/85.8 |

FOREIGN PATENT DOCUMENTS

| | | |
|---|---|---|
| 0272858 | 6/1988 | European Pat. Off. |
| 0286447 | 10/1988 | European Pat. Off. |
| 9003735 | 4/1990 | PCT Int'l Appl. |

OTHER PUBLICATIONS

Golding et al., *Chem. Abstracts* (1988) 108(23):534 (Abstract No. 203058w).
Schrier et al., *J. Immunol.* (1989) 142(4):1166–1176.
Hoffmann et al., *Proc. Natl. Acad. Sci.* (1991) 883060–883064.
Sinha, et al., 1990, "Autoimmune Diseases: The Failure of Self Tolerance," Nature 248: 1380–1387.
Hoffmann, et al., 1986, "A new symmetry: A anti-B is anti-(B anti-A), ... " J. Immunol. 137(1): 61–8.
Shearer, *Mount Sinai J. Med.* (1986) 53(8):609–615.
Andrieu et al., *AIDS Research* (1986) 2(3):163–174.
Martinez et al., *Lancet* (1988) I(8583):454–456.
Siliciano et al., *Cell* (1988) 54:561–575.
Hoffmann *The Semiotics of Cellular Communication in the Ummune System*, Sercarz, E. E. et al., eds. (1988) Springer Verlag, pp. 257–271.
Lanzavecchia *Research in Immunology* (1989) 140:99–103.
Calabrese, *Clin. Lab. Med.* (1988) 8:269–279.
Habeshaw et al., *J. Acqu. Imm. Def.* (1989) 2(5):457–468.
Morrow et al., *Clin. Immunol. and Immunopath.* (1990) 57:in press.
Grant et al., *Cellular Basis of Immune Modulation* Caplan J. G. et al., eds., (1989) A. R. Liss, Inc., New York, pp. 481–484.
Hoffmann et al., *Canadian Research* (1988) 21:16–23.
Grant et al., *J. Immunol.* (1990) 144(4):1241–1250.

(List continued on next page.)

*Primary Examiner*—Christine M. Nucker
*Assistant Examiner*—Lynette F. Smith
*Attorney, Agent, or Firm*—Townsend and Townsend

[57] ABSTRACT

Substances that bind to alloimmune-immunogen-absorbed (AIA) sera have been found to be effective in the prevention and therapy of autoimmune disease. It is conjectured that the mechanism involves indirect stimulation of suppressor T cells resulting in stabilization of the immune system. The administration of such substances is expected to be useful in the prevention and treatment of diseases that involve a failure of the immune system to distinguish adequately between self and nonself, including autoimmune diseases and immunodeficiency diseases.

12 Claims, 6 Drawing Sheets

OTHER PUBLICATIONS

Hoffman et al., "Mathematical and Statistical Approaches to AIDS Epidemiology", Castillo-Chavez ed., *Lect. Notes in Biomat.* (1989) 83:386-405.
Hoffmann et al., "Idiotype Networks in Biology and Medicine" Osterhaus et al., eds., (1990) Elsevier, Amsterdam, pp. 295-299.
Hoffmann et al., *Immunology Letters* (1989) 22:83-90.
Hoffmann et al., *Theoretical Immunology* A. S. Perelson, ed. Addison-Wesley, Redwood City, Calif. (1988) pp. 291-319.
Cohen *Sci. Amer.* (1988) 258:34-42.
Shearer et al., *Annals N.Y. Acad. Sci.* (1985) 437:49-57.
Ziegler et al, *Clin. Immunol. and Immunopathol.* (1986) 41:305-313.
Elkins, et al., 1987 "Prior exposure to subimmunogenic amounts . . . " Infect. & Imm. 55:3085-3092.
Klasse et al., 1988 "Presence of antibodies to a putatively . . . " PNAS 55; 5225-5229.
Kion and Hoffmann, *Science* 253:1138-1140 (1991).

IMMUNE SYSTEM STABILIZERS FOR PREVENTION AND THERAPY OF DISORDERS ASSOCIATED WITH IMMUNE SYSTEM DISFUNCTION

CROSS-REFERENCE TO RELATED APPLICATIONS

This is a continuation-in-part of U.S. patent application Ser. No. 07/551,262, filed Jul. 11, 1990, now abandoned.

TECHNICAL FIELD

The invention relates to the application of certain substances to prevention and therapy of conditions that reflect an immunodeficiency involving a failure to adequately distinguish between self and non-self. Administration of sub-immunogenic amounts of substances that are immunoreactive with alloimmune sera that have been absorbed against the immunogen used in producing the alloimmune serum can prevent immune system disfunction, and such substances can also be used in therapy. The mechanism underlying this invention is thought to involve indirect stimulation of suppressor T cells of the immune system.

BACKGROUND ART

No consensus exists concerning the mechanisms involved in the regulation of the immune system. One view is that the immune system is a network of cells that not only recognize foreign substances, but also recognize and regulate each other. Hoffmann et al. have developed a model of immune system regulation that provides the conceptual framework from which the present invention emerged (Hoffmann, 1975; 1978; 1980; 1981; 1982; 1988; 1990; Gunther and Hoffmann, 1982, Hoffmann et al., 1988; Hoffmann and Grant, 1989; Grant et al., 1989; Hoffmann and Grant, 1990; Hoffmann et al., 1990). The model includes suppressor T cells with idiotypes that have similarity to class II MHC in the sense that both class II MHC and the suppressor T cell iiotypes in question have complementarity to helper T cell idiotypes (Hoffmann, 1988; Hoffmann et al., 1988).

AIDS is an immunodeficiency disease that results in the development of both autoimmunity (Ziegler and Stites, 1986; Shearer, 1986; Andrieu, et al., 1986; Martinez-A , et al., 1988; Siliciano et al., 1988; Grant et al., 1990) and cancers such as Kaposi's sarcoma and lymphomas. A unifying aspect of the occurence of both cancer and autoimmunity in AIDS may be a failure of the immune system to distinguish properly between self and non-self. The possible importance of autoimmunity in AIDS is illustrated by the fact that 31 similarities have been noted between AIDS and systemic lupus erythematosus (Kaye, 1989). Shearer suggested that alloimmunity may be important in AIDS pathogenesis (Shearer, 1983), while Ziegler and Stites proposed the first autoimmunity model of AIDS pathogenesis based on network ideas (Ziegler and Stites, 1986). Hoffmann et al. have developed a model of AIDS pathogenesis based on autoimmunity, alloimmunity and network ideas (Hoffmann, 1988; Hoffmann et al.; 1988; Hoffmann and Grant, 1989; Hoffmann, Kion and Grant, 1988; Hoffmann et al., 1989; Grant et al., 1989; Hoffmann, Kion and Grant, 1990; Hoffmann, 1990). This model has been called the MIAMI model of AIDS pathogenesis, which is short for MHC-Image-Anti- MHC-Image; the model involves synergy between MHC-image immunity and anti-MHC-image immunity in destabilizing the immune system. Experimental evidence supporting such a model of pathogenesis has been recently been obtained for the MRL mouse (Kion and Hoffmann, 1990). The MRL mouse is a model for the disease systemic lupus erythematosus. Several cancers occur in AIDS, including Kaposi's sarcoma and lymphomas. According to the immune surveillance theory of oncogenesis, cancers occur when the immune system fails to recognize them as abnormal or "foreign", and does not eliminate them. Hence the formation of at least some cancers may be a consequence of a failure in self-nonself discrimination by the immune system.

A variety of conditions similar to AIDS exist in animals and may have etiologies similar to that of AIDS (Salzman, 1986).

Stimulation of the immune system in a way that enhances and/or stabilizes its ability to distinguish between self and non-self, will prevent some failures of the immune system including AIDS and systemic lupus erythematosus.

DISCLOSURE OF THE INVENTION

The invention in one aspect is directed to specifically modify the status of the immune system to prevent and treat diseases in which the immune system of a vertebrate subject fails to adequately distinguish between self and nonself. Such diseases include AIDS, autoimmune diseases such as systemic lupus erythematosus, and cancers associated with immunodeficiencies. The method involves the administration of a substance that stabilizes the immune system network (an "immune system stabilizer"). The immune system stabilizer of this invention is a substance that reacts with AIA sera (alloimmune-immunogen-absorbed sera, that is, alloimmune sera absorbed with the immunogen used in producing the sera) more strongly than with normal (non-immune) serum from the same species. Methods of treatment and prevention are the same, except that they may involve different regimens of administration of the immune system stabilizer.

While not intending the invention to be bound by any theory, the immune system stabilizer is believed to contain an antigenic component that indirectly or directly stimulates suppressor T cells. In our network view of the immune system, at least some suppressor T cells are believed to stabilize the immune system network through their interactions with helper T cells (see Hoffmann 1988; Hoffmann et al., 1988).

Substances that react with alloimmune-immunogen-absorbed ("AIA") sera include gp120 of the human immunodeficiency virus ("HIV") and p24 of HIV. As partial proof of principle, both of these substances have been found to inhibit the progression of autoimmune disease in a murine model of autoimmunity, namely the MRL-1pr/1pr mouse.

In another respect, the invention is directed to pharmaceutical compositions suitable for the conduct of the method of the invention.

BRIEF DESCRIPTION OF THE DRAWINGS

FIG. 1A shows that gp120 of HIV binds more strongly to murine AIA (alloimmune-immunogen-absorbed) sera than to normal mouse serum. FIG. 1B shows that p24 of HIV binds more strongly to murine AIA (alloimmune-immunogen-absorbed) sera than to normal mouse serum.

Figure 1A:
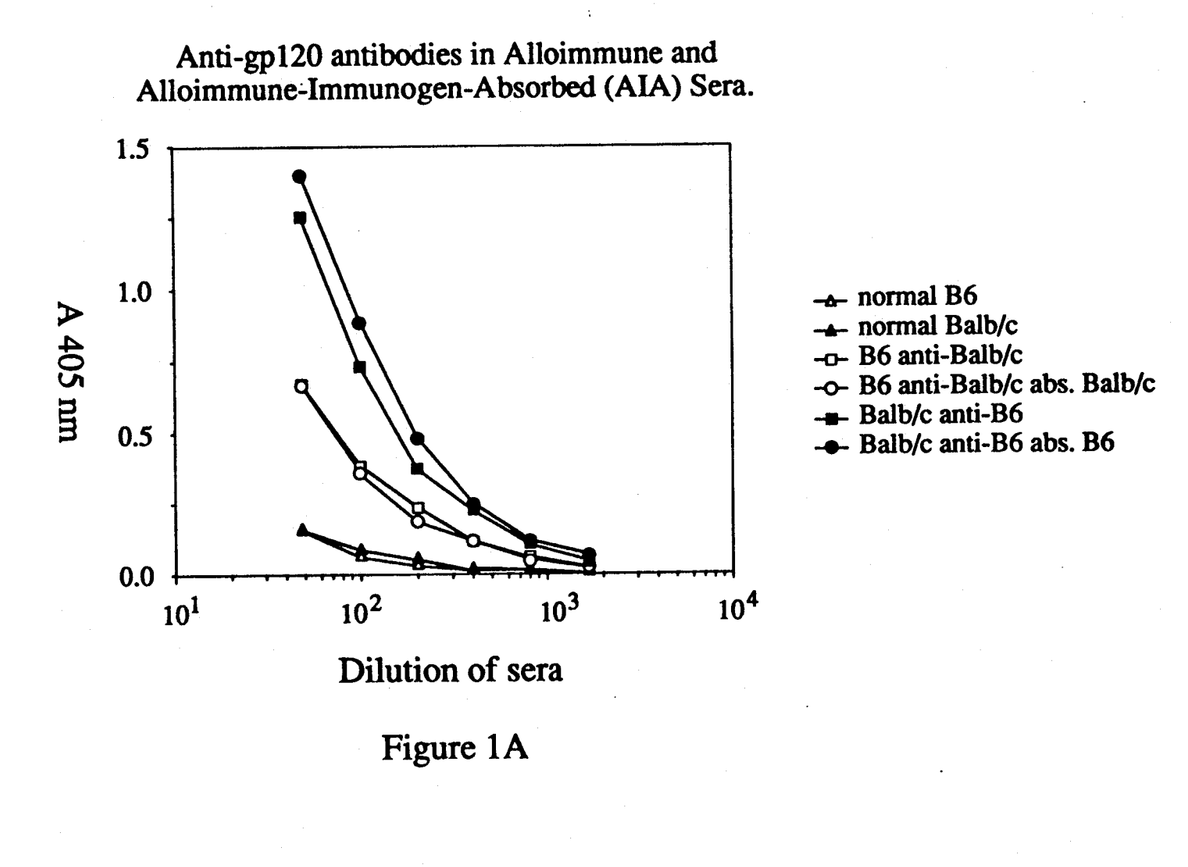
Figure 1B:
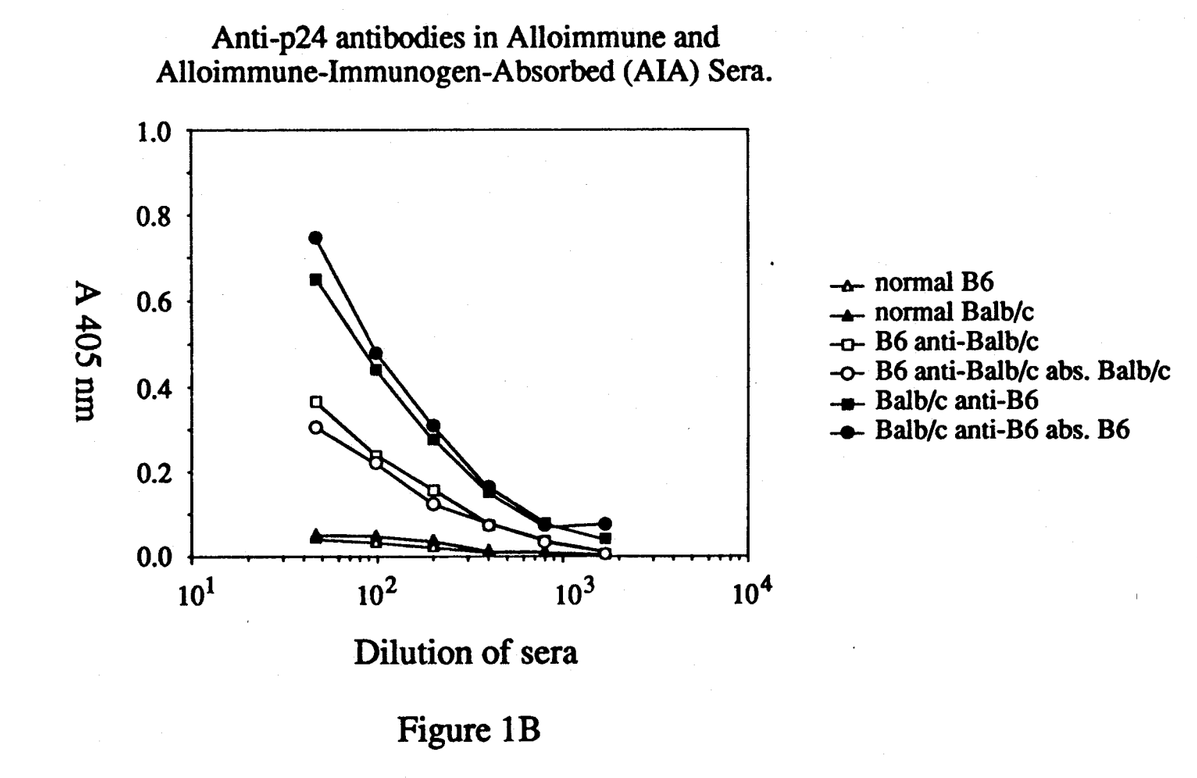
Figure 2A:
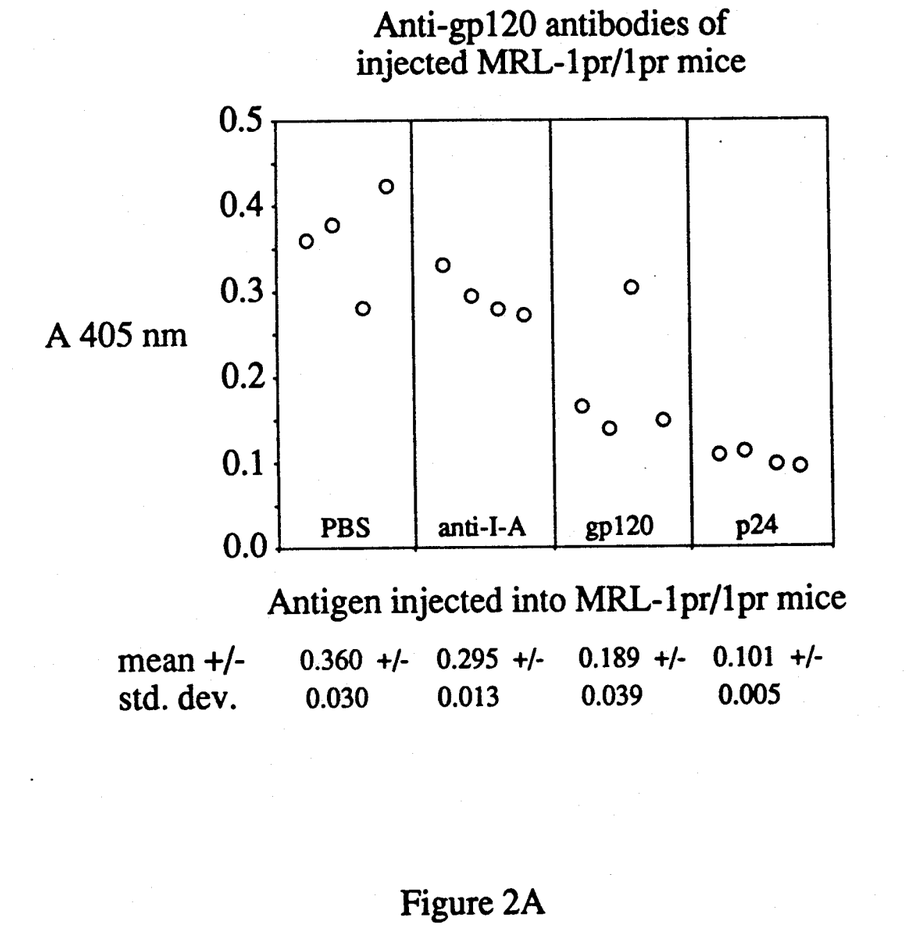
Figure 2B:
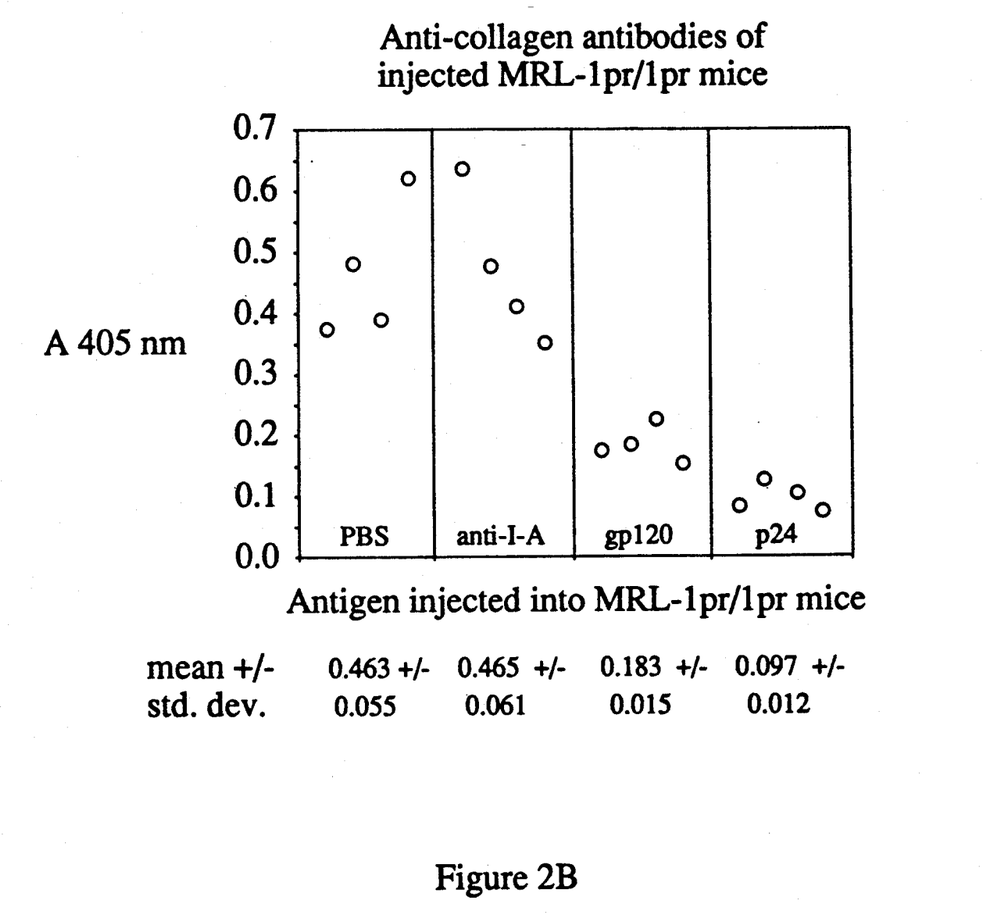
Figure 2C:
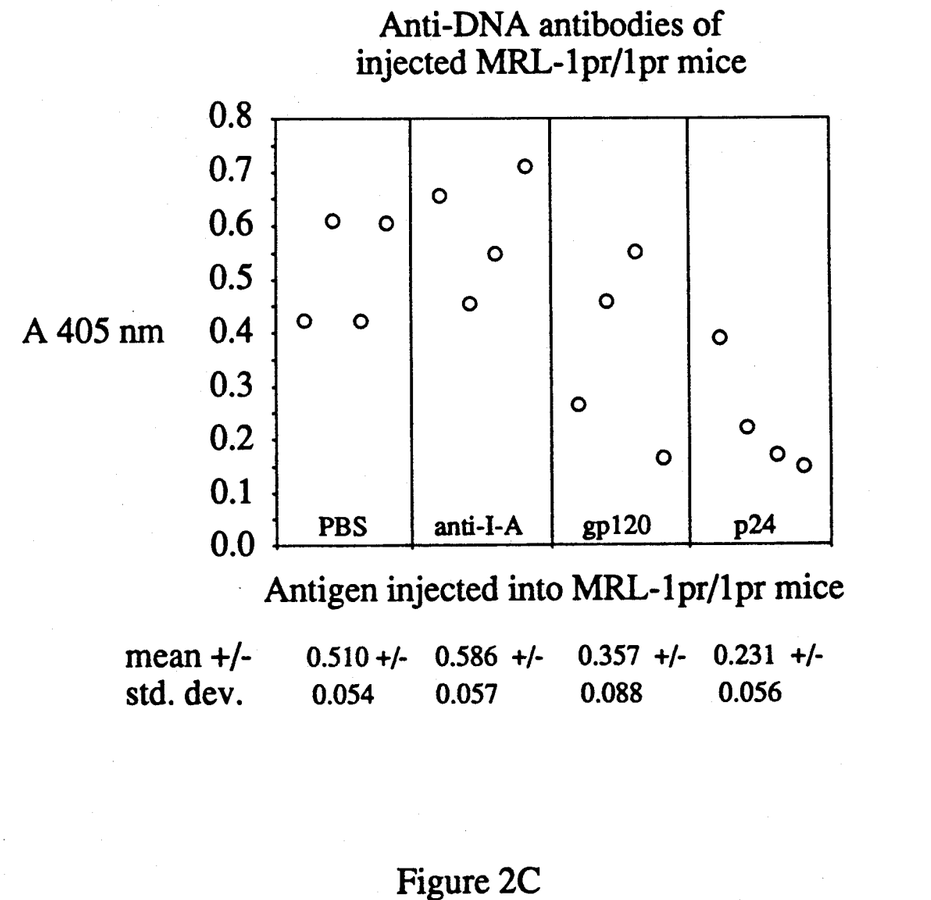

FIG. 2 shows the level of various diagnostic antibodies (anti-DNA, anti-collagen and anti-gp120) in a strain of mice that is a model for autoimmunity following injections of gp120 and p24 from HIV, with the levels for similar mice injected with phosphate buffered saline as a negative control. FIG. 2A shows that the level of anti-gp120 in these mice is reduced (compared with the level in controls) as a result of the injections; FIG. 2B shows that the level of anti-collagen is reduced as a result of such injections, and FIG. 2C shows that the level of anti-DNA antibodies in these mice is reduced as a result of such injections.

Figure 3:
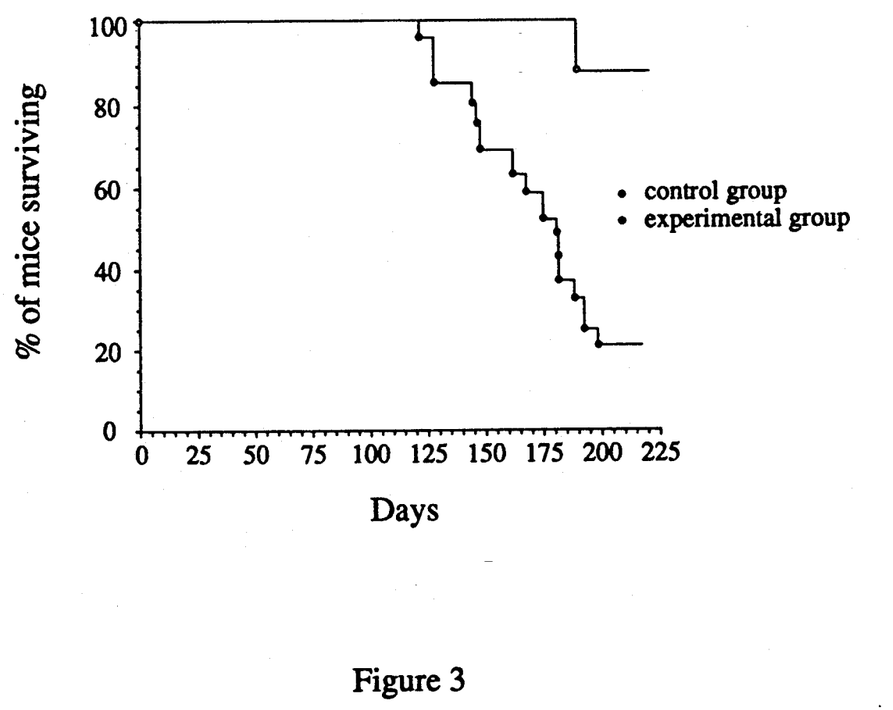

FIG. 3 shows survival data (as of mid-Dec., 1990) for mice used in the experiment of FIG. 2. The "experimental group" data are pooled data for the p24 and gp120-injected mice; four mice received p24 of HIV, and four mice received gp120 of HIV. The control mice received either nothing (15 mice) or phosphate buffered saline (4 mice from group 1 of the FIG. 2 experiment). At the time of submission, the p24-injected mice are all alive (4/4), and 3 of the 4 gp120-injected mice are alive, in contrast to only about 20% of the control mice being alive at the corresponding time point.

MODES OF CARRYING OUT THE INVENTION

The invention is directed to a method to modify the immune system of a subject and thus to (a) prevent diseases involving a failure of the immune system to adequately distinguish between self and nonself, and (b) provide a therapy for such conditions. This is done by administration(s) of a substance(s) that reacts with AIA (alloimmune-immunogen-absorbed) sera, in a way that does not induce immunity to the said substance, but that is found empirically to stabilize the system in a comparatively healthy state.

Preparation of AIA Alloimmune-immunogen-absorbed sera or AIA is prepared from the sera of a vertebrate that has been made hyperimmune with respect to allogeneic lymphocytes as detailed in Hoffmann et al., 1986, incorporated herein by reference. Alloimmune murine sera are produced by first immunizing mice with 6 weekly injections of $5 \times 10^7$ allogeneic lymphoid cells (lymph node, spleen and thymus) in phosphate buffered saline, pH 7.2 (PBS). The mice are first bled 7 days after the sixth injection, and thereafter they are injected with $10^7$ allogeneic lymphoid cells 7 days prior to subsequent bleedings at 2 week intervals. The antisera are pooled, heat inactivated at 56° C. for 30 minutes and stored at −20° C. until use. AIA is produced by absorbing the alloimmune serum by 5 serial absorptions against $2 \times 10^9$ glutaraldehyde-fixed lymphocytes (of the strain used in the immunizations) per ml. of serum. Each absorption is done at room temperature for 1 hour with occasional mixing. Such absorptions remove all detectable cytotoxic activity against the immunizing cells in the serum.

Human AIA can be obtained, for example, from the alloimmune serum of a monogamous, multiparous mother with a high titre of immunity to her husband's cells. The absorption against the husband's lymphocytes is done as described above for immune murine serum.

Either murine AIA or human AIA can be used to screen candidate antigens. Since murine AIA reacts with p24 and gp120 of the human virus HIV, and since these human viral components provide protection and therapy for a murine autoimmune disease, it is possible that murine AIA and human AIA may be approximately equally suitable for screening for AIA antigens for use in humans.

In addition, our idiotypic network model of AIDS pathogenesis (Hoffmann, Kion and Grant, 1990) suggests that HIV components have determinants that are cross-reactive with MHC-image determinants on the T cell receptors of certain suppressor T cells. There may be considerable cross-reactivity between MHC-image determinants in various species. Gp120 and p24 of HIV are examples of substances that are obtained from a human virus yet bind to murine AIA, and that have been shown to work in prevention and therapy of murine autoimmunity (see below). This suggests that there is a considerable amount of interspecies cross-reactivity in AIA, and murine AIA may well be a suitable reagent for screening for human immune system stabilizers.

Screening Candidate Antigens Against AIA Serum

An ELISA assay is conveniently used. ELISA plates are coated with the substance to be tested, the plates blocked with 5% casein, then incubated with murine AIA serum. Bound antibodies are detected using biotinylated goat anti-mouse IgG and avidin-alkaline phosphatase. An analogous assay is also conducted but substituting normal non-immune serum from the same species as the AIA serum for the AIA serum in the assay. Substances which react more strongly with the AIA serum than with the normal serum are useful antigens. Other protocols and detection systems can be used as is understood in the art.

Selection of Candidate Substances For Binding To AIA Serum

Suitable candidates are substances for which there is some reason to believe that they may have shapes that mimic the shape of major histocompatability complex antigens For example, there is much evidence suggesting that some HIV components have shapes that mimic MHC class II antigens (discussed in Hoffmann et al., 1990).

Illustrative AIA-reactive substances include gp120 and p24 of HIV (see below). They may also include gp41 and Nef of HIV, since gp41 has been reported to have serological cross-reactivity with class II MHC (Golding et al., 1989), and Nef has some sequence homology with class II MHC (Vega et al., 1990).

Another class of AIA-reactive substances are some of the antibodies present in alloimmune sera, or monoclonal antibodies derived from alloimmune vertebrates. Antibodies contained within one AIA often react with antibodies in another AIA (Kion and Hoffmann, unpublished). For example, if a mouse of strain A is made immune to lymphocytes from mice of a strain B (that has a different MHC haplotype), and if a mouse of strain B is similarly made immune to lymphocytes from mice of strain A, each of the resulting AIA sera contains antibodies that react with the other AIA. This is due to the fact that AIA typically contain both MHC-image and anti-MHC-image antibody activities, and MHC-image antibodies in one AIA typically react with anti-MHC-image antibodies in another AIA.

Still another class of AIA-reactive substances ar anti-I-J antibodies. These are a class of murine antibodies that are present in some alloimmune sera and that react mainly with suppressor T cells. It has been suggested that anti-I-J antibodies are anti-MHC-image antibodies (Hoffmann, 1988; Hoffmann et al., 1988). We, find that monoclonal anti-I-J antibodies bind to AIA (Kion and Hoffmann, unpublished), and they may be effective reagents in the context of this invention.

Utility and Administration

The antigens immunoreactive with AIA serum are immune system stabilizers and are administered in subimmunogenic doses to suitable subjects As the dosage levels are subimmunogenic, the risk factors in administering these materials as prophylactics to the general population are very low. Particularly preferred subjects are those in the more elderly population, as the ability of the immune system to discriminate between self and non-self deteriorates with age. This is evidenced by an increasing amount of anti-self antibodies in the immune responses of older people and an increase with age and the prevalence of autoimmune phenomena in cancers.

The immune system stabilizers of the invention are also useful therapeutic agents in treatment of subjects with known autoimmune conditions. Thus, the invention protocol can be used to treat various conditions affecting the immune system, such as acquired immunodeficiency syndrome (AIDS) and systemic lupus erythematosus (SLE) and other autoimmune diseases such as myasthenia gravis, rheumatoid arthritis, and the like. The dosage levels are at a subimmunogenic level and are thus expected to be in the range of $10^4$–$10^6$ fold less than amounts required for an immunogenic dose. The appropriate dosage levels for a particular subject can be determined by reference to a suitable animal model. For example, in determining dosage levels suitable for the treatment of human diseases such as AIDS and SLE, reference can be had to animal models to determine the relative amounts of antigen to be administered.

Administration is by any systemic route, and is typically by injection, such as intramuscular, subcutaneous, intraperitoneal, or intravenous injection. Suitable formulations for injection are understood in the art and include solutions or suspensions of the antigen in a compatible aqueous medium such as Hank's solution or Ringer's solution. Systemic administration can also be effected by transmucosal or transdermal delivery using appropriate penetrants and absorption mediators, such as bile salts, fusidates and various detergents. Transmucosal administration is typically effected by nasal sprays, suppositories, or introduction into the lungs. In addition, when properly formulated, the immune system stabilizers of the invention may be administered orally. For oral administration, however, the formulation must provide a means for transport of the drug to the bloodstream.

Suitable formulations for a particular mode of administration are designed using techniques within ordinary skill of the art. Such formulations are cataloged, for example, in "Remington's Pharmaceutical Sciences," latest edition, Mack Publishing Co., Easton, Pa. All of the formulations may contain various excipients which are benign and pharmaceutically acceptable, including various carriers, buffers, stabilizing agents, wetting agents and the like.

The particular formulation, dosage level and mode of administration chosen will depend on the nature of the condition to which the immune stabilization is directed, on the general health and nature of the subject, and on the judgment of the practitioner. Suitable subjects include not only humans, but animals; the immune system stabilizers may also be appropriately formulated for veterinary use.

EXAMPLES

The following examples illustrate but do not limit the invention.

Example 1

Gp120 and p24 of HIV bind to murine AIA sera. Alloimmune sera were raised in Balb/c and C57BL/6 (B6) mice by repeated reciprocal immunizations using B6 and Balb/c lymphoid cells. The sera of the resulting alloimmune mice were then tested for the presence of antibodies immunoreactive with gp120 and p24 of HIV. Antibodies immunoreactive with both of these viral components were detected in alloimmune mice but not in non-immune controls. These results are shown in FIGS. 1A and 1B for anti-gp120 and anti-p24 respectively. The triangles show the results for the non-immune control sera, the open squares and full squares are for B6 anti-Balb/c and Balb/c anti-B6 immune sera respectively, and the circles are for alloimmune-immunogen-absorbed sera, namely B6 anti-Balb/c absorbed with Balb/c (open circles) and Balb/c anti-B6 absorbed with B6 cells (full circles). It is apparent that absorption with the immunogen (which removes the cytotoxic activity of the sera) does not remove the anti-gp120 or anti-p24 immuno-reactivity.

Example 2

Prevention of Autoimmunity in MRL-1pr/1pr Mice: MRL-1pr/1pr is a mouse strain that develops a lupus-like autoimmune disease. The AIA-binding substances gp120 and p24 of HIV inhibit the formation of autoantibodies in MRL-1pr/1pr mice. MRL-1pr/1pr mice were immunized intraperitoneally with the following antigens at ages 3 weeks and 4 weeks. (PBS is phosphate buffered saline).

Group 1: 0.2 ml PBS alone

Group 2: 10 ng of anti-I-$A^k$ monoclonal antibody in 0.2 ml PBS.

Group 3: 10 ng of gp120 of HIV in 0.2 ml PBS.

Group 4: 10 ng of p24 of HIV in 0.2 ml PBS.

All mice were bled at 4 weeks after the second injection, and the sera were obtained as individual samples, heat inactivated at 56° C. for 30 minutes.

FIG. 2 shows the level of various diagnostic antibodies in a strain of mice that is a model for autoimmunity following injections of gp120 and p24 from HIV, with the levels for similar mice injected with phosphate buffered saline as a negative control. FIG. 2A shows that the level of anti-gp120 in these mice is reduced (compared with the level in controls) as the result of the injections; FIG. 2B shows that the level of anti-collagen is reduced as a result of such injections, and FIG. 2C shows that the level of anti-DNA antibodies in these mice is reduced as a result of such injections.

Example 3

The AIA-binding substances gp120 and p24 of HIV enhance longevity. MRL-1pr/1pr mice injected with AIA-binding material only at 3 weeks and 4 weeks of age (the mice used in the preceding experiment) are being monitored for longevity. This experiment is still in progress (Dec. 13, 1990), but it is already clear that especially mice in the groups 3 and 4 of the above experiment are living longer than control mice. Most dramatically, in the group of four that were injected with p24

(group 4 above), 4 of 4 are alive and well at day 211, when about 80% of the control mice are dead. In the gp120 group (group 3 above) 3 of 4 mice are alive at 211 days. In FIG. 3, the "experimental group" is pooled data for the p24 and gp120 injected groups of mice. The "control group" of FIG. 3 shows data for the PBS-injected group (group 1 above) pooled with a larger group of 15 MRL-1pr/1pr mice that received no injections. This combined group of mice have a median life span of 178 days, and only 4 of 19 were alive at 205 days.

Example 4

Therapy for autoimmunity in MRL-1pr/1pr mice. Three month old MRL-1pr/1pr mice exhibit a significant amount of autoimmunity. Weekly injections of 10 ng of gp120 of HIV beginning at age 3 months have been found to markedly inhibit the development of lymphadenopathy in these mice (relative to phosphate buffered saline injected controls), and after eleven weeks of these injections these mice appear much healthier than the controls.

References

Andrieu, J. M., Even, P. and Venet, A. (1986) AIDS Research 2, 163–174.

Calabrese, L. H. (1988) Clin. Lab. Med. 8, 269.

Golding, H., Shearer, G. M., Hillman, K., Lucas, P., Manishewitz, J., Zajac, R. A., Clerici, M., Gress, R. E., Boswell, R. N., and Golding, B. (1989) J. Clin. Invest 83, 1430–1435.

Grant, M. D., Weaver, M. S., Tsoukas, C. and Hoffmann, G. W. (1990): J. Immunol., 144, 1241–1250.

Grant, M., Kion, T. A., Forsyth, R. B., and Hoffmann, G. W. (1989) in J. G. Kaplan and D. R. Green, eds., A. R. Liss, Inc., New York, pp. 481–484.

Gunther, N. and Hoffmann, G. W. (1982), Journal of Theoretical Biology, 94, 815–855.

Habeshaw J. A. & Dagleish, A. (1989) J. AIDS, 2, 457–468.

Hoffmann, G. W. (1975) European Journal of Immunology, 5, 638–647 (1975).

Hoffmann, G. W. (1978) in "Theoretical Immunology" G. I. Bell, A. S. Perelson and G. H. Pimbley (eds.) Marcel Dekker, N.Y., pp. 571–602.

Hoffmann, G. W. (1980) Contemp. Top. Immunobiol. 11, 185–226.

Hoffmann, G. W. (1981) in The Immune System, Festschrift in Honour of Niels Kaj Jerne, on the Occasion of his 70th Birthday (I. Lefkovits and C. Steinberg, Eds.) Karger, Basel, vol. I, pp. 28–34. Hoffmann, G. W. (1982) in Regulation of Immune Response Dynamics, C. DeLisi and J. Hiernaux (Eds.), CRC Press, pp. 137–162.

Hoffmann, G. W. (1988) in "The Semiotics of cellular Communication in the Immune System" (E. Sercarz, F. Celada, N. A. Mitchison and T. Tada, Eds.) Springer-Verlag, New York, pp. 257–271.

Hoffmann, G. W. (1990) Res. in Immunol., in press.

Hoffmann, G. W. and Grant, M. D. (1989) in "Mathematical and Statistical Approaches to AIDS Epidemiology," C. Castillo-Chavez, Ed., Lecture Notes in Biomathematics, vol. 83, Springer-Verlag, 1989, pp. 386–405.

Hoffmann, G. W. and Grant, M. D. (1990) in "Idiotype Networks in Biology and Medicine", A. D. M. E. Osterhaus and F. G. C. M. UytdeHaag, Eds., Elsevier, Amsterdam, pp. 295–299.

Hoffmann, G. W. and Tufaro, F. (1989) Immunol. Letters, 22, 83–90.

Hoffmann, G. W., Cooper-Willis, A. and Chow, M. (1986) J. Immunol. 137, 61–68.

Hoffmann, G. W., Grant M. and Kion, T. A. (1988) Canadian Research, 21, No. 6, pp. 16–23.

Hoffmann, G. W., Kion, T. A. and Grant, M. D. (1990) "An Idiotypic Network Model of AIDS Immunopathogenesis" Proc. Nat. Acad. Sci. (USA), in press.

Hoffmann, G. W., Kion, T. A., Forsyth, R. B., Soga, K. G. and Cooper-Willis, A. (1988) in "Theoretical Immunology, Part Two", A. S. Perelson, Ed., Santa Fe Institute Series "Studies in the Science of Complexity", Addison Wesley Publishing Company, 291–319.

Kaye, B. R., (1989) Ann. Int. Med. 111, 158–167.

Kion, T. A. and Hoffmann, G. W. (1990), submitted for publication.

Lanzavecchia, A. (1989) Research in Immunol. 140, 99–103.

Martinez-A, C., Marcos, M. A. R., de la Hera, A., Marquez, C., Alonso, J. M., Toribio, M. L. and Coutinho, A. (1988) Lancet, Feb. 27, 1988.

Morrow, W. J. W., Isenberg, D. A., Sobol, R. E., Stricker, R. B. and Kieber-Emmons, T. Clin. Immunol. & Immunopath. in press.

Salzman, L. A. (1986) "Animal Models of Retrovirus Infection and their Relationship to AIDS." (L. A. Salzman, editor) Academic Press.

Shearer, G. M. (1983) N. Engl. J. Med. 308, 223–224.

Shearer, G. M. (1986) Mount Sinai J. Med. 53, 609–615.

Siliciano, R. F., Lawton, T., C. Knall, C., Karr, R. W. Bermann, P., Gregory, T. & Reinherz, E. L. (1988) Cell 54:561.

Vega, M. A., Guigo, R. and Smith, T. F. (1990) Nature, 345, 26.

Ziegler J. L. and Stites, D. P. (1986) Clin Immunol. and Immunopath. 41, 305–313.

I claim:

1. A method for treating or inhibiting the development of symptoms of an autoimmune disease in a subject, which method comprises administering to the subject a subimmunogenic amount of an antigen more immunoreactive with alloimmune-immunogen-absorbed (AIA) serum as compared to nonimmune serum of the same species as the AIA serum.

2. The method of claim 1 wherein the AIA serum is murine.

3. The method of claim 1 wherein the AIA serum is human.

4. The method of claim 1 wherein the subject is human.

5. The method of claim 1 wherein the subject is a nonhuman vertebrate.

6. The method of claim 1 wherein the antigen comprises gp41 from HIV.

7. A method to activate T-suppressor cells in a subject susceptible to or suffering from symptoms of an autoimmune disease, which method comprises administering to a subject in need thereof a subimmunogenic amount of an antigen more immunoreactive with alloimmune-immunogen-absorbed (AIA) serum as compared to nonimmune serum of the same species as the AIA serum.

8. The method of claim 1, wherein the autoimmune disease is systemic lupus erythematosus.

9. The method of claim 7, wherein the autoimmune disease is systemic lupus erythematosus.

10. A method to inhibit the production of autoantibodies in a subject susceptible to or suffering from an autoimmune disease which method comprises administering to the subject a subimmunogenic amount of an antigen which is more immunoreactive with alloimmune-immunogen-absorbed (AIA) serum as compared to nonimmune serum of the same species as the AIA serum.

11. The method of claim 10 wherein the autoantibodies are anti-collagen.

12. The method of claim 10 wherein the autoantibodies are anti-DNA.

* * * * *